(12) United States Patent
Tabiti et al.

(10) Patent No.: US 7,118,867 B2
(45) Date of Patent: Oct. 10, 2006

(54) QUANTITATIVE MULTIPLEX PCR WITH HIGH DYNAMIC RANGE

(75) Inventors: Karim Tabiti, Poecuing (DE); Gisela Betzl, Moosweg (DE); Richie Soong, Parap, NJ (US); Randy P. Rasmussen, Salt Lake City, UT (US); Deepika Marine Desilva, Salt Lake City, UT (US); John G. Ward, Salt Lake City, UT (US); Hallegh Page Millward, Riverton, UT (US)

(73) Assignees: Roche Diagnostics Corporation, Indianapolis, IN (US); Idaho Technology, Inc., Salt Lake City, UT (US)

( * ) Notice: Subject to any disclaimer, the term of this patent is extended or adjusted under 35 U.S.C. 154(b) by 562 days.

(21) Appl. No.: 10/300,576

(22) Filed: Nov. 19, 2002

(65) Prior Publication Data

US 2003/0215830 A1   Nov. 20, 2003

Related U.S. Application Data

(60) Provisional application No. 60/331,791, filed on Nov. 20, 2001.

(51) Int. Cl.
   *C12Q 1/68*   (2006.01)
   *C12P 19/34*   (2006.01)
(52) U.S. Cl. .......................................... 435/6; 435/91.2
(58) Field of Classification Search .................. 435/6, 435/91.1, 91.2
   See application file for complete search history.

(56) References Cited

U.S. PATENT DOCUMENTS 5,976,842 A * 11/1999 Wurst ........................ 435/91.2

FOREIGN PATENT DOCUMENTS

| EP | 0 942 917 | 9/1999 |
| EP | 01 098 993 | 5/2001 |
| WO | WO 200005409 A1 * | 2/2000 |

OTHER PUBLICATIONS

Dostal et al. ("An Improved Method for Absolute Quantification of mRNA Using Multiplex Polymerase Chain Reaction: Determination of Renin and Angiotensinogen mRNA Levels in Various Tissues" Analytical Biochemistry. 1994. vol. 223: pp. 239-250).*

Kellogg et al ("TaqStart Antibody: Hot Start PCR Facilitated by a Neutralizing Monoclonal Antibody Against Taq DNA Polymerase" BioTechniques. 1994. vol. 16, No. 6: pp. 11-34-1137).*

Lin et al. ("Inhibition of Multiple Thermostable DNA Polymerases by a Heterodimeric Aptamer" Journal of Molecular Biology. 1997. 271: pp. 100-111).*

Vet et al. ("Multiplex detection of four pathogenic retroviruses using molecular beacons" Proc. Natl. Acad. Sci. May 1999. vol. 96: pp. 6394-6399).*

Wong et al. ("Monitoring mRNA Expression by Polymerase Chain Reaction: The "Primer-Dropping" Method" Analytical Biochemistry. 1994. 223: pp. 251-258).*

Henegariu et al. ("Multiplex PCR: Critical Parameters and Step-by-Step Protocol" BioTechniques. Sep. 1997. 23: pp. 504-511).*

Hahn, S., et al., 2000, "Multiplex and Real-Time Quantitative PCR on Fetal DNA in Maternal Plasma, A comparison with Fetal Cells Isolated from Maternal Blood," *Annals New York Academy of Sciences*, 906:148-152.

"Highly Efficient and Specific RT-PCR with a new combination of QIAGEN enzymes", *QIAGEN NEWS, Online*, 1999, 4:15-16.

"FastStart Taq DNA Polymerase: end your chase for the most specific hot start PCR results", *Roche Diagnostics GmbH, Roche Molecular Biochemicals Online*, Aug. 2000.

Ryncarz, A., et al., 1999, "Development of a High-Throughput Quantitative Assay for Detecting Herpes Simplex Virus DNA in Clinical Samples", *Journal of Clinical Microbiology*, 37(6):1941-1947.

Vet, J., et al., 1999, Multiplex detection of four pathogenic retroviruses using molecular beacons, *Proc Natl Acad Sci, USA*, 96:6394-6399.

* cited by examiner

*Primary Examiner*—Kenneth R. Horlick
*Assistant Examiner*—Christopher M Babic
(74) *Attorney, Agent, or Firm*—Townsend and Townsend and Crew LLP; Charles M. Doyle

(57) ABSTRACT

The invention provides a method for quantitative multiplex PCR of two targets whereby one target is present in at least 100-fold molar excess over that of the other target. The method further comprises the addition of a thermostable DNA polymerase with a final concentration of at least 0.5 units/μl.

10 Claims, 6 Drawing Sheets

| | PCR Type | CK20 copies | PBGD copies |
|---|---|---|---|
| ---o--- | individual | $10^2$ | $10^4$ |
| —o— | individual | $10^4$ | $10^4$ |
| —o— | individual | $10^6$ | $10^4$ |
| ------- | multiplex | $10^2$ | $10^4$ |
| — — | multiplex | $10^4$ | $10^4$ |
| ——— | multiplex | $10^6$ | $10^4$ |

| Plasmid copies | | Crossing Point | |
|---|---|---|---|
| CK20 | PBGD | CK20 | PBGD |
| $10^2$ | $10^4$ | 32.81 | 32.40 |
| $10^4$ | $10^4$ | 25.90 | 31.75 |
| $10^6$ | $10^4$ | 19.06 | 32.66 |
| $10^8$ | $10^4$ | 11.14 | 33.60 |

| | Plasmid copies | | Crossing Point | |
|---|---|---|---|---|
| | CK20 | PBGD | CK20 | PBGD |
| ——— | $10^2$ | $10^4$ | 32.81 | 32.40 |
| —◇— | $10^4$ | $10^4$ | 25.90 | 31.75 |
| —□— | $10^6$ | $10^4$ | 19.06 | 32.66 |
| —◇— | $10^8$ | $10^4$ | 11.14 | 33.60 |

QUANTITATIVE MULTIPLEX PCR WITH HIGH DYNAMIC RANGE

This application claims the benefit of priority under 35 U.S.C. § 119 of co-pending provisional application No. 60/331,791, filed Nov. 20, 2001, the contents of which are hereby incorporated by reference therein.

BACKGROUND OF THE INVENTION

1. Field of the Invention

The current invention relates to the field of real-time PCR. More particular, the current invention relates to the field of quantifying nucleic acids, in particular cellular mRNA.

2. Description of the Related Art

Quantification of mRNA has been an outstanding task in the field of molecular biology in order to obtain information on the expression of particular genes of interest. Conventionally, this has been done either by means of semi-quantitative Northern Blot analysis or semi-quantitative RNAse protection assays.

In addition, availability of the PCR technology and especially availability of Reverse Transcriptase PCR (RT-PCR), have enabled a more sensitive quantitative detection of low abundance mRNAs from small samples. In RT-PCR, a single-stranded cDNA is produced first from the mRNA to be analyzed using a reverse transcriptase. Subsequently, a double-stranded DNA amplification product is generated with the aid of PCR.

A distinction is made between two different variants of this method. In the so-called relative quantification the ratio of the expression of a certain target RNA is determined relative to the amount of RNA of a so-called housekeeping gene which is assumed to be constitutively expressed in all cells independent of the respective physiological status. Hence the mRNA is present in approximately the same amount in all cells. The advantage of this is that different initial qualities of the various sample materials and the process of RNA preparation have no influence on the particular result. However, an absolute quantification is not possible with this method.

Alternatively, the absolute amount of RNA used can be determined with the aid of standard nucleic acids of a known copy number and amplification of a corresponding dilution series of this standard nucleic acid. When using internal standards i.e. by amplifying the standard and target nucleic acid in one reaction vessel, standards have to be used that have different sequences compared to the target nucleic acid to be analyzed in order to be able to distinguish between the amplification of the standard and target nucleic acid.

Further progress could be achieved by applying methods of kinetic real-time PCR which allow for a kinetic monitoring of the amplification reaction and thus more accurate quantification of particular target molecules.

In this case, the formation of PCR products is monitored in each cycle of the PCR. The amplification is usually measured in thermocyclers which have additional devices for measuring fluorescence signals during the amplification reaction. A typical example of this is the Roche Molecular Biochemicals LightCycler (Cat. No. 20110468). The amplification products are for example detected by means of fluorescent labeled hybridization probes which only emit fluorescence signals when they are bound to the target nucleic acid or in certain cases also by means of fluorescent dyes that bind to double-stranded DNA.

A defined signal threshold is determined for all reactions to be analyzed and the number of cycles Cp required to reach this threshold value is determined for the target nucleic acid as well as for the reference nucleic acids such as the standard or housekeeping gene. The absolute or relative copy numbers of the target molecule can be determined on the basis of the Cp values obtained for the target nucleic acid and the reference nucleic acid (Gibson, U. E., et al., Genome Res 6 (1996) 995–1001.; Bieche, I., et al., Cancer Res 59 (1999) 2759–65.; WO 97/46707). Such methods are also referred to as a real-time PCR.

SUMMARY OF INVENTION

In summary, in all the described methods for the quantification of a nucleic acid by PCR, the copy number formed during the amplification reaction is always related to the copy number formed of a reference nucleic acid which is either a standard or an RNA of a housekeeping gene.

In many cases it is of outstanding interest to quantify more than one nucleic acid target within one reaction vessel in a so-called multiplex approach. This is the case, for example, for embodiments of relative quantification, wherein the expression level of a certain mRNA is determined as compared to the expression level of a typical housekeeping gene (Meijerink, J., et al., J Mol Diag 3 (2001) 55–61). Furthermore, the simultaneous quantification of different mRNA species may be of interest, in case more complex expression patterns need to be analyzed in order to investigate or analyze complex cellular processes.

The major drawback with multiplex PCR is that in many cases, a nucleic acid target species with low abundance as compared to a second nucleic acid target species can not be amplified with reasonable efficiency, such that a respective amplification signal corresponding to the low abundance nucleic acid target is not detected (for example: Bercovich, D., et al., Biotechniques 27 (1999) 762–770). In other words, the dynamic range of nucleic acid quantities that can be detected in a multiplex approach in many cases is very limited.

In this context it is important to note that the dynamic range of a multiplex approach is usually independent from the absolute values of the different target nucleic acids to be detected, but almost exclusively depends on the molar ratio of the different target nucleic acids present in the sample to be analyzed.

Surprisingly, however, the dynamic range that can be obtained seems to be assay- and target dependent: Vet, J. A., et al., Proc Natl Acad Sci USA 96 (1999) 6394–9 disclose a sophisticated multiplex assay for the detection of 4 pathogenic Retroviruses using Molecular Beacons wherein the dynamic range is $10^4$. Similarly, Director-Myska, A. E., et al., Environ Mol Mutagen 37 (2001) 147–154 disclose a specific quantitative plasmid mixture analysis using the fluorogenic 5' nuclease format (TaqMan format), wherein a dynamic range of $10^3$ to $10^4$ is achieved.

Tucker, R. A., et al., Mol Diagn 6 (2001) 39–47 disclose a TaqMan real-time PCR assay for relative quantification of HPV 16 versus beta-Actin mRNA, wherein amplification of $5 \times 10^4$ Actin copies does not affect amplification of HPV 16 RNA, however, on the other hand, 100 fold eccess of HPV 16 mRNA template inhibits amplification of beta-Actin. Especially from this example, it can be concluded that the molecular basis for problems in obtaining a reasonable dynamic range in multiplex PCR is far from being understood.

Attempts in the art have been made in order to overcome this problem by an appropriate adjustment of primer concentrations. Halminen, M., et al., Cytokine 11 (1999) 87–93 disclose relative quantification of Interferon-Gamma mRNA and Interferon-4 mRNA compared to beta-Actin expression, wherein limited amounts of beta-Actin primers are used. Similarly, Bercovich, D., et al., Biotechniques 27 (1999) 762–770 recommend inclusion of increased amount of primers of the under-represented target nucleic acid or, alternatively, lowering the annealing temperature of such multiplex reactions.

All the methods disclosed in the art, however, require a time extensive adaptation of PCR conditions as a pre-requisite of appropriate accurate measurement of nucleic acid concentrations. Therefore, there exists a need in the art for a standardized multiplex PCR protocol, which provides a reasonable broad dynamic range without specific adaptation with regard to the nature of the target or the concentration of the primers used.

BRIEF DESCRIPTION OF THE FIGURES

FIG. 2: Monoplex and Multiplex amplification of various ratios of CK20 and PBGD with 0.0825 U/µl Taq DNA Polymerase FIG. 3: Multiplex amplification of CK20/PBGD with increasing amounts of Taq Polymerase

FIG. 4: Multiplex amplification with and without hot start PCR using increasing amounts of Polymerase FIG. 5: Extend of dynamic range which can be obtained with excess hot start Polymerase

BRIEF DESCRIPTION OF THE INVENTION

Figure 1:
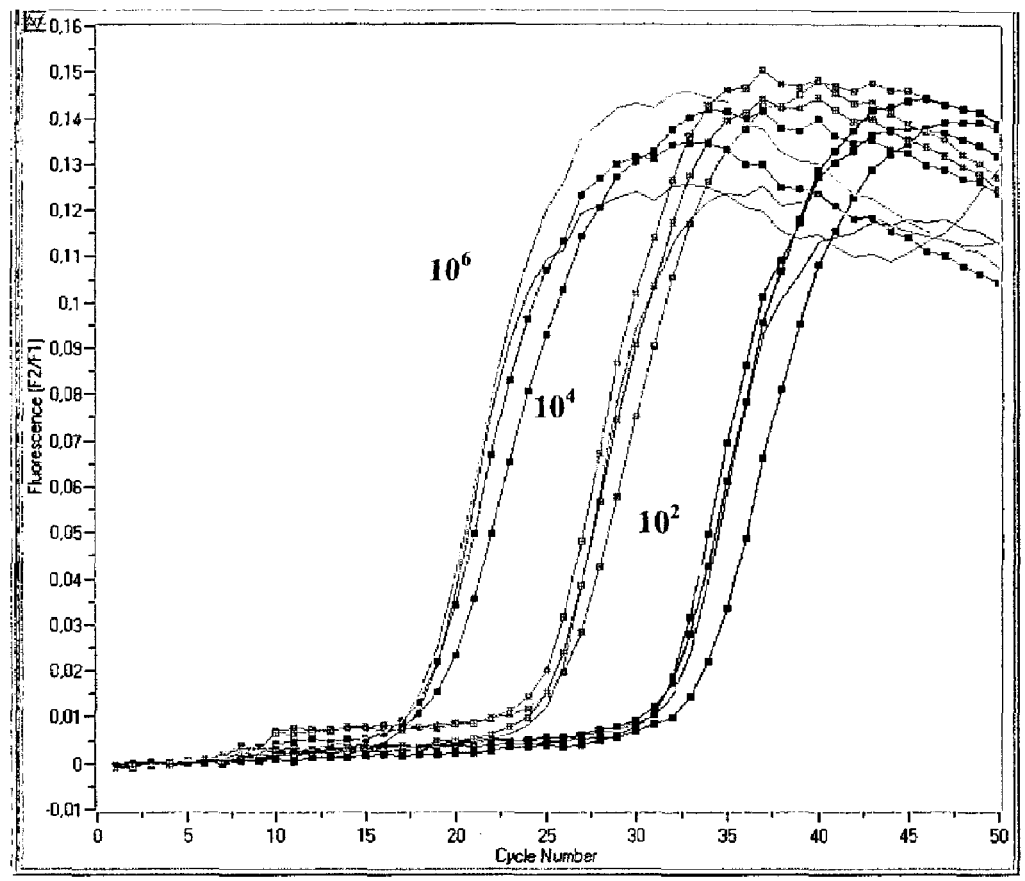
FIG. 1: Monoplex amplification $10^2$, $10^4$, and $10^6$ copy numbers of CK 20 each were amplified with either 0.0825 U/µl, 0.165 U/µl, 0.33 U/µl or 0.66 U/µl Polymerase.

Accordingly, the new invention provides a method for quantitative multiplex PCR with a dynamic range of at least $10^2$, wherein a thermostable DNA Polymerase with a final concentration of at least 0.5 units/µl is used. Preferably, a dynamic range of at least $10^3$ and most preferably, a dynamic range of at least $10^4$ is obtained.

More specifically, the invention is directed to a method for quantification of at least a first and a second nucleic acid in a sample by means of PCR, which is characterized in that the original concentration of the first nucleic acid in the sample is in excess of more than a factor of 100 as compared to the original concentration of the second nucleic acid, comprising addition of a first primer pair for amplification of the first nucleic acid, addition of a second primer pair for amplification of a second nucleic acid, and amplification of the 2 nucleic acids by a thermostable DNA Polymerase. According to the invention, said thermostable DNA Polymerase is present in a concentration of at least 0.5 units/µl reaction, and amplification of the second nucleic acid is not inhibited to less than 10% as compared to amplification of the second nucleic acid with the second primer pair in the absence of said first primer pair.

It has also been proven to be additionally advantageous, if a PCR according to the present invention is performed by means of hot start, i.e. by appropriate inhibition of primer dimer formation. In this case, DNA Polymerase according to the invention is present in a concentration of at least 0.25 units/µl.

The inventive method is especially applicable, if PCR amplification is monitored in real time. Preferably the amplification products obtained are each detected by at least one fluorescently labeled hybridization probe.

In a specific embodiment, two adjacently hybridizing probes are used for each target nucleic acid, and each probe is appropriately labeled with a fluorescent moiety such that said moieties are able to perform fluorescence resonance energy transfer upon hybridization (FRET-hybridization probes).

In another preferred embodiment which may also include real time monitoring, the amplification reactions are performed by means of rapid thermocycling, wherein one cycle is less than one minute.

In a further aspect, the invention is directed to kits comprising reagents for performing the inventive method(s). Such a kit preferably comprises a master mix which comprises a thermostable DNA Polymerase in a sufficient concentration to provide a final concentration of said thermostable DNA Polymerase of at least 0.5 units/µl or, alternatively at least 0.25 units/µl and additional compounds required for a hot start amplification protocol.

DETAILED DESCRIPTION OF THE INVENTION

The new invention provides a method for quantitative multiplex PCR with a dynamic range of at least $10^2$, wherein a thermostable DNA Polymerase with a final concentration of at least 0.5 units/µl is used. Preferably, a dynamic range of at least $10^3$ and most preferably, a dynamic range of at least $10^4$ is obtained.

It is also important to note, that the inventive method is applicable for a broad variety of different target concentrations. In this context, it will also be shown in the examples that the same dynamic range according to the invention is obtained at least in case the target nucleic acids to be amplified within a multiplex assay are present in copy numbers between $10^2$ and $10^8$.

In the context of the present invention, one unit of thermostable DNA polymerase is defined as the amount of enzyme that incorporates 20 nmol of total desoxyribonucleoside-triphosphates into acid precipitable DNA within 60 min at 65° C. Under standard assay conditions.

These conditions are 67 mM Tris/HCl, pH8.3/25° C., 5 mM $MgCl_2$, 10 mM Mercaptoethanol, 0.2% Polydocanol, 0.2 mg/ml Gelatine 0.2 mM each dATP, dGTP, dTTP, and 0.1mMdCTP, pH8.3/25° C.

Activity can be measured by incubation of M13mp9ss, M13 primer (17 mer) and 1 µCi(alpha-32-P) dCTP with suitable dilutions of Taq Polymerase in a 50 µl incubation buffer at 65° C. for 60 min. Amount of incorporated dNTPs is then determined by trichloracetic acid precipitation.

Multiplex PCR according to the invention as well as disclosed in the prior art is defined as a PCR assay, wherein in one reaction vessel, more than one nucleic acid target sequence is amplified in the presence of more than one (at least two) pair(s) of amplification primers.

The invention is explicitly directed to a method for quantification of at least a first and a second nucleic acid in a sample by means of PCR. For many applications, the target nucleic acids to be analyzed are derived from total cellular RNA or total poly-A RNA (mRNA). For such an RT-PCR analysis, quantification is achieved by means of an RNA dependent cDNA synthesis prior to the amplification reaction itself. The cDNA synthesis reaction may either be performed using a specific Reverse Transcriptase enzyme followed by amplification with a conventional thermostable DNA Polymerase. Alternatively, cDNA synthesis and RT-PCR may be performed using a thermostable enzyme possessing both RNA dependent Reverse Transcriptase and DNA dependent DNA Polymerase activity.

Not withstanding the foregoing, genomic DNA may also be analyzed in a multiplex approach according to the invention e.g. for determination of gene dosages or numbers of repetitive sequences.

In the context of the present invention the term "quantification of a nucleic acid" may comprise different possibilities such as absolute determination of the copy numbers of multiple nucleic acids present in a sample as compared to an absolute reference standard, or, alternatively, determination of a relative value as compared to other nucleic acids found in the same sample.

Of course, it is also within the scope of the invention if not only two rather than multiple target nucleic acids are amplified. Regarding the number of targets to be analyzed, no upper limit has been determined experimentally yet. In experimental practice, however, the inventive method is only limited by the number of possibilities for detecting different amplified fragments.

The original concentrations of the different target nucleic acids of interest according to the invention may differ from each other at least by a factor of 100. In addition, it has also been proven by the inventors that the new method is broadly applicable to situations, wherein the starting concentrations of the different target nucleic acids may differ from each other by a factor of 1 000 or even 10 000. Respective data are shown in the examples below.

A typical assay according to the invention will comprise a pair of amplification primers for each target nucleic acid to be quantified, a suitable buffer, Deoxy-Nucleoside-triphosphates, and a thermostable DNA Polymerase with a concentration of at least 0.5 units/µl reaction. Independent from the type and number of amplification targets to be quantified, the high enzyme concentration will guarantee that the amplification of low abundance targets is not more than 10% inhibited by the presence of other amplified targets as compared to amplification of the low abundance nucleic acid target in a monoplex approach.

In contrast the maximum concentration of Polymerase that can be applied is usually 10 units/µl. Concentrations around 5 units/µl, i. e. between 3 and 7 units/µl or preferably around 2 units/µl, i. e. between 1 and 3 µl also in most cases work very well.

In addition, amplification may be performed in the presence of agents which provide a means for detection of the amplification products. For example, the reaction vessel may already contain appropriate hybridization probes for homogenous real time detection of amplification products. Preferably, these probes may be appropriately labeled with fluorescent moieties.

It has also been proven to be additionally advantageous, if a PCR according to the present invention is performed by means of hot start, i.e. by appropriate inhibition of primer dimer formation. Such a formation of primer dimers is mainly due to residual Polymerase activity at ambient temperatures prior to the thermocycling reaction itself. As opposed to regular amplification protocols, during a hot start protocol, Polymerase activity is activated only after initial heating, thereby excluding any activity at lower temperatures inductive to the annealing or amplification of non-specific product (e.g. primer dimers). This step turned out to be more critical in the context of a multiplex PCR where there is an increased load of oligonucleotides (primers, fluorescent probes, amplified product) in the same reaction vessel.

It has been proven by the inventors that application of an arbitrarily chosen hot start technique reduces the requirement of excess amounts of thermostable Polymerase by about a factor of two. Therefore, according to the invention, a reliable multiplex PCR protocol with a dynamic range of at least $10^2$ comprises the usage of a final DNA Polymerase concentration of at least 0.25 units/µl in combination with an arbitrary hot start technique.

Consequently, the present invention is also directed to a method for quantification of at least a first and a second nucleic acid in a sample by means of PCR, characterized in that the original concentration of the first nucleic acid in the sample is in excess of more than a factor of 100 as compared to the original concentration of the second nucleic acid, comprising addition of a first primer pair for amplification of the first nucleic acid, addition of a second primer pair for amplification of a second nucleic acid, amplification of the 2 nucleic acids by a thermostable DNA Polymerase, wherein said thermostable DNA Polymerase is present in a concentration of at least 0.25 units/µl reaction, and wherein amplification of the second nucleic acid is not inhibited to less than 10% as compared to amplification of the second nucleic acid with the second primer pair in the absence of said first primer pair, and wherein a hot start PCR is performed.

Primer dimer formation, therefore, may be inhibited by several methods known in the art:

For example, the DNA Polymerase is reversibly inactivated as a result of a chemical modification. More precisely, heat labile blocking groups are introduced into the Taq DNA Polymerase which render the enzyme inactive at room temperature. These blocking groups are removed at high temperature during a pre-PCR step such that the enzyme is becoming activated. Such a heat labile modification, for example can be obtained by coupling Citraconic Anhydride or Aconitric Anhydride to the Lysine residues of the enzyme (U.S. Pat. No. 5,677,152). Enzymes carrying such modifications are meanwhile commercially available as Amplitaq Gold (Moretti, T., et al., Biotechniques 25 (1998) 716–22. or FastStart DNA Polymerase (Roche Molecular Biochemicals).

Alternatively, extension of non-specifically annealed primers has been shown to be inhibited by the addition of short double stranded DNA fragments (Kainz, P., et al., Biotechniques 28 (2000) 278–82.). In this case, primer extension is inhibited at temperatures below the melting point of the short double stranded DNA fragment, but independent from the sequence of the competitor DNA itself. Even more specific, oligonucleotide Aptamers with a specific sequence resulting in a defined secondary structure may be used. Such Aptamers have been selected using the SELEX Technology for a very high affinity to the DNA Polymerase (U.S. Pat. No. 5,693,502), (Lin, Y. Jayasena, S. D., J Mol Biol 271 (1997) 100–11). The presence of such Aptamers within the amplification mixture prior to the actual thermocycling process itself again results in a high affinity binding to the DNA Polymerase and consequently a heat labile inhibition of its activity.

Another approach to achieve heat labile inhibition of Taq DNA Polymerase is the addition of monoclonal antibodies raised against the purified enzyme (Kellogg, D. E., et al., Biotechniques 16 (1994) 1134–7; Sharkey, D. J., et al., Biotechnology (N Y) 12 (1994) 506–9). Like the oligonucleotide Aptamers, the antibody binds to Taq DNA Polymerase with high affinity at ambient temperatures in an inhibitory manner. The complex is resolved in a preheating step prior to the thermocycling process itself. This leads to a substantial time consuming prolongation of the amplification as a whole, especially if protocols for rapid thermocycling are applied (WO 97/46706).

Regardless, whether a hot start technique is applied or not, the inventive method is especially applicable, if PCR amplification is monitored in real time resulting in a homogenous detection format. Thus, the amplification products obtained are preferably detected by at least one fluorescently labeled hybridization probe. The instrumental basis for such real time monitoring is provided by commercially available instruments like the Roche Light Cycler (Roche Molecular Biochemicals), the ABI Prism 7700 (Perkin Elmer), or the iCycler (BioRad).

As indicated, fluorescently labeled hybridization probes may be used for real time monitoring. Those hybridization probes used for the inventive method according to the invention are usually single-stranded nucleic acids such as single-stranded DNA or RNA or derivatives thereof or alternatively PNAs which hybridize at the annealing temperature of the amplification reaction to the target nucleic acid. These oligonucleotides usually have a length of 20 to 100 nucleotides.

The labeling can be introduced on any ribose or phosphate group of the oligonucleotide depending on the particular detection format. Labels at the 5' and 3' end of the nucleic acid molecule are preferred.

The type of label must be detected in the real-time mode of the amplification reaction. This is not only possible for fluorescently labeled probes but also possible with the aid of labels that can be detected by NMR. Methods are particularly preferred, however in which the amplified nucleic acids are detected with the aid of at least one fluorescent labeled hybridization probe.

Many test procedures are possible. The following three detection formats have proven to be particularly useful in connection with the present invention, but shall not be understood as limiting the inventive scope.

(i) FRET Hybridization Probes

For this test format two single-stranded hybridization probes are used simultaneously which are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

Among all detection formats possible within the scope of the present invention, this "FRET-hybridization probe" has been proven to be highly sensitive, exact and reliable. Alternatively, it is also possible to use a fluorescent-labeled primer and only one labeled oligonucleotide probe (Bernard, P. S., et al., Anal Biochem 255 (1998) 101–7.).

(ii) TaqMan Hybridization Probes

A single-stranded hybridization probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'–3' exonuclease activity of the Taq Polymerase during the subsequent elongation phase. As a result the excited fluorescent component and the quencher are spatially separated from one another and thus a fluorescence emission of the first component can be measured.

(iii) Molecular Beacons

These hybridization probes are also labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

It is also within the scope of the invention, if real time PCR is performed using a double stranded nucleic acid binding moiety. For example, the respective amplification product can also be detected according to the invention by a fluorescent DNA binding dye which emits a corresponding fluorescence signal upon interaction with the double-stranded nucleic acid after excitation with light of a suitable wavelength. The dyes SybrGreen and SybrGold (Molecular Probes) have proven to be particularly suitable for this application. Intercalating dyes can alternatively be used. However, for this format, in order to discriminate the different amplification products, it is necessary to perform a respective melting curve analysis (U.S. Pat. No. 6,174,670).

In another preferred embodiment which may also include real time monitoring, the amplification reactions are performed by means of rapid thermocycling, wherein one cycle is less than one minute. The instrumental basis for such a rapid thermocycling is provided e.g. by the LightCycler (Roche Molecular Biochemicals) and disclosed in WO 97/46707 and WO 97/46712. According to the present invention, the annealing of primers is not the rate limiting step of quantitative amplification of target nucleic acids being present in the sample with only low abundance. Therefore, the time parameters for a respective multiplex thermocycling protocol in order to amplify low abundance parameters don't need to be amended as compared to any kind of thermocycling protocols known in the art.

In a further aspect, the invention is directed to kits comprising reagents for performing the inventive method(s). More specifically, such a kit may comprise a master mix which can be used for amplification in such a way that only the sample to be analyzed, suitable primers, and some water to adjust the reaction volume need to be added prior to the thermocycling reaction itself.

According to the invention, the master mix comprises a thermostable DNA Polymerase in a sufficient concentration to provide a final concentration of said thermostable DNA Polymerase of at least 0.5 units/µl. Parameter specific kits may additionally contain primers with respective sequences. These oligonucleotides even may be included into the master mix.

Furthermore, such a kit may contain reagents suitable for homogeneous detection of products generated by real time PCR, for example fluorescently labeled hybridization probes or double strand DNA binding entities. Like the respective primers, in some cases they also may become included into the master mix.

Alternatively, an inventive kit may comprise a master mix for hot start PCR. Such a master mix would include a thermostable DNA Polymerase in a sufficient concentration to provide a final concentration of said thermostable DNA Polymerase of at least 0.25 units/µl, and an additional compound to enable hot start PCR. Such a compound which would inactivate Polymerase activity at ambient temperatures, for example may be an anti-Polymerase antibody, or a Polymerase binding nucleic acid aptamer.

In yet another embodiment, the inventive kit may comprise a master mix for hot start PCR which includes a thermostable DNA Polymerase in a sufficient concentration to provide a final concentration of said thermostable DNA Polymerase of at least 0.25 units/µl that is chemically modified and thus inactive at ambient temperatures unless the Polymerase is heated in order to remove the chemical modification.

It has also been proven to be advantageous, if the kit contains either a known amount of standard DNA in order to generate a dilution series for a standard curve, or, alternatively a calibrator sample which may be used in order to determine the efficiency of a certain type of amplification reaction.

The following examples, references, sequence listing and figures are provided to aid the understanding of the present invention, the true scope of which is set forth in the appended claims. It is understood that modifications can be made in the procedures set forth without departing from the spirit of the invention.

EXAMPLE 1

Real Time PCR of CK20 and PBGD Plasmid DNA

To demonstrate the validity of the invention, cytokeratin 20 (CK20), a gene studied for the detection of disseminated tumor cells and porphorynbilinogen deaminase (PBGD), commonly used as a housekeeping gene were chosen as amplification targets.

Partial fragments of the Cytokeratin 20 (CK20) and porphoryinbilinogen deaminase (PBGD) genes were cloned into separate pT3T7 plasmid vectors (Roche Molecular Biochemicals). Copy numbers of linearized plasmid DNA were estimated spectrophotometry with the assumption that 1 mole is equivalent to $6 \times 10^{23}$ copies. CK20 and PBGD Plasmid DNA mixtures were prepared by dilutions using a diluent consisting of MS2 RNA (10 ng/µl) in 10 mM Tris-HCl, pH 8.5.

Kinetic PCR was conducted on a LightCycler instrument (Roche Molecular Biochemicals). A typical PCR assay consisted of 1 µl DNA, 1×Detection Mix, 1×Reaction buffer, 4 mM magnesium chloride and varying amounts of Taq Polymerase (all from Roche Diagnostics, Mannheim, Germany) adjusted with water to a 10 µl volume in one reaction capillary.

For regular monoplex and multiplex PCR, the reaction buffer and the unmodified Taq Polymerase from the Light-Cycler—DNA Master Hybridisation Probes Kit (Roche Molecular Biochemical, Cat. No. 2 015 102) were used.

The 10×Detection Mixes for CK20 and PBGD each consisted of 5 µM of each primer (forward and reverse), 2 µM of each hybridization probe (Flourescein and LC-Red640 or fluorescein and Lcred705 labeled), 0.05% Brij-35 in 10 mM Tris-HCl, pH 8.5 buffer. For Multiplex PCR, an additional 1×Detection mix was included into the reaction capillary. The following primer and hybridization probes sequences were used:

```
CK20 Forward primer:
5'ATCAAGCAGTGGTACGAAAC-3'                                (Seq. Id. No: 1)

CK20 Reverse primer:
5'-AGGACACACCGAGCATTT-3'                                 (Seq. Id. No: 2)

CK20 probe1:
5'-ATTACAGACAAATTGAAGAGCTGCG-flourescein-3'              (Seq. Id. No: 3)

CK20 probe2:
5'-LCRed640AGTCAGATTAAGGATGCTCAACTGCphosphate-3'         (Seq. Id. No: 4)

PBGD Forward primer:
5'-GCGGAGCCATGTCTGGTAA-3'                                (Seq. Id. No: 5)

PBGDReverse primer:
5'-CCAGGGTACGAGGCTTTCAA-3'                               (Seq. Id. No: 6)

PBGD probe1:
5'-GAGAGTGATTCGCGTGGGTACCCG.fluorescein-3'               (Seq. Id. No: 7)

PBGD probe2:
5'-LCRed705.AGAGCCAGCTTGCTCGCATACAGAC.phosphate-3'       (Seq. Id. No: 8)
```

The labeling of a hybridization probe for CK20 PCR with LCRed640 and for PBGD PCR with LCRed 705 allowed simultaneous monitoring of each reaction in separate channels. Crosstalk in fluorescence between channels 2 (LCRed640) and 3 (LCRed705) was compensated for by using the LightCycler—Color Compensation Set (Roche Molecular Biochemicals).

Regular PCR cycling conditions consisted of an initial 94° C. incubation for 1 minute followed by 50 cycles of 94° C. for 0 seconds, 55° C. for 10 seconds and 72° C. for 10 seconds and was concluded with 40° C. for 30 seconds.

Crossing points for each reaction were determined by the LightCycler Analysis software using the second derivative maximum function with an arithmetic baseline setting.

EXAMPLE 2

Excessive Polymerase does not Increase Performance of a Monoplex PCR Assay

Real time PCR of $10^2$, $10^4$ and $10^6$ copies CK 20 was performed in a monoplex set up according to example 1 with increasing amounts of either 0.0825 U/µl, 0.165 U/µl, 0.33 U/µl or 0.66 U/µl Fast Start Polymerase (Roche Molecular Biochemicals). Results are shown in FIG. 1. As can be seen, an increase in enzyme concentration does not result in a lower Cp value, since the fluorescent signal curves for each copy number identified were basically identical regardless of the enzyme concentration used (left: $10^6$ copies, middle: $10^4$ copies, right: $10^2$ copies). It has to be concluded that for a monoplex PCR, i.e. amplification of only one target nucleic acid, the amplification reaction is not enhanced by an excess of Polymerase, even if target nucleic acid is initially present in high copy numbers.

EXAMPLE 3

Targets of relatively low abundance are not quantitatively amplified within a multiplex PCR approach FIG. 2 shows typical results of monoplex PCRs of CK20 and PBDG respectively according to example 1 as compared to a multiplex approach by simply combining the primer sets and fluorescent probe sets for kinetic PCR) of two individual PCRs into a single PCR (multiplex PCR) according to example 1 using 0.0825 U/µl Taq Polymerase.

Figure 2A:
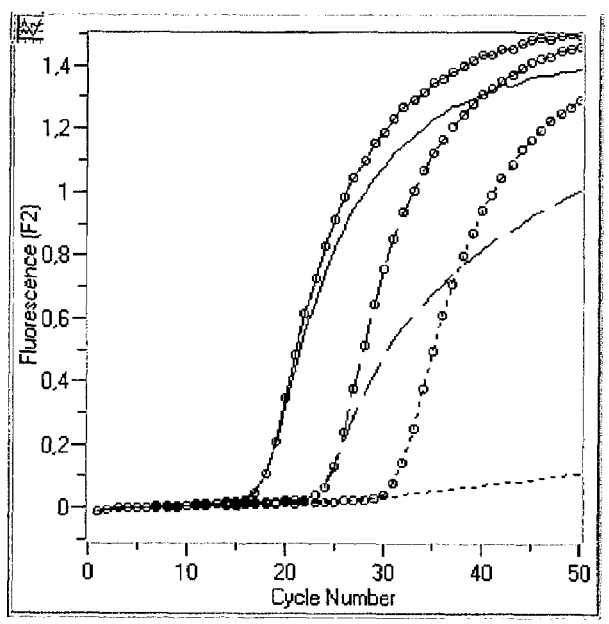
FIG. 2a: amplification of CK20—monoplex assay and multiplex set up
Figure 2B:
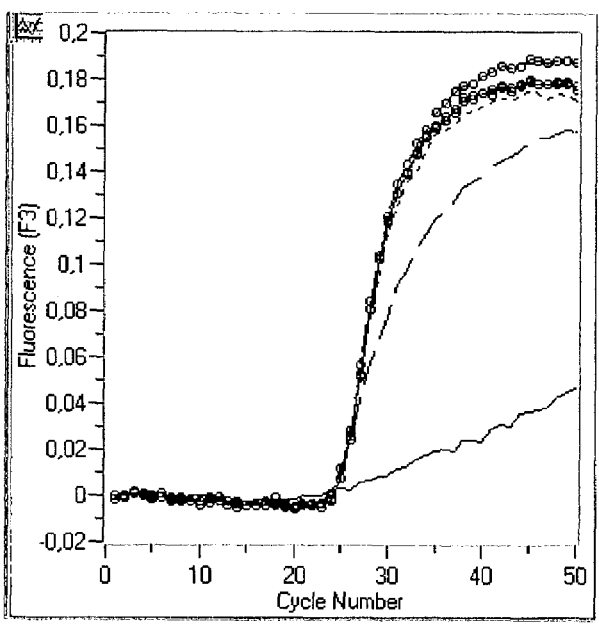
FIG. 2b: amplification of PBGD—monoplex assay and multiplex set up

The different template nucleic acids for the reactions include three plasmid mixtures containing CK20/PBGD copy amounts of $10^2/10^4$, $10^4/10^4$ and $10^6/10^4$ respectively. In the same PCR run, the reaction efficiency of amplifying CK20 in an individual PCR with no competing reaction (FIG. 2a), and in a multiplex PCR with a background PBGD PCR occurring in the same reaction vessel, is monitored in channel 2 (FIG. 2a). Simultaneously, the reaction efficiency for amplifying PBGD in an individual and multiplex PCR is monitored in channel 3 (FIG. 2b).

The results show a significant reduction in the gradient of the target PCR exponential phase curve in a multiplex PCR when compared to an individual PCR, especially when the copy numbers of template for the background reaction exceed 100 times that of the target reaction. This is namely the amplification of $10^2$ CK20 copies in the presence of amplifying $10^4$ PBGD copies and $10^4$ PBGD copies in the presence of amplifying $10^6$ CK20 copies. These results obtained according to methods known in the art suggest that under typical PCR conditions known in the art, the dynamic range is unambiguously less than a factor of 100.

EXAMPLE 4

Figure 3A:
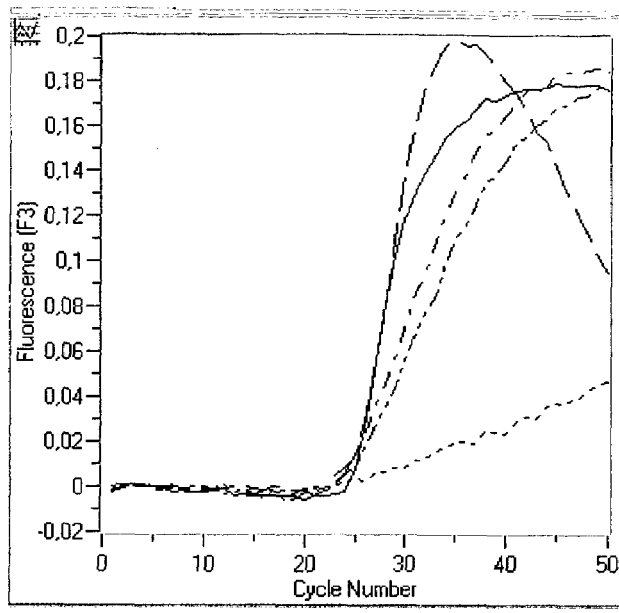
FIG. 3a: CK20
Figure 3B:
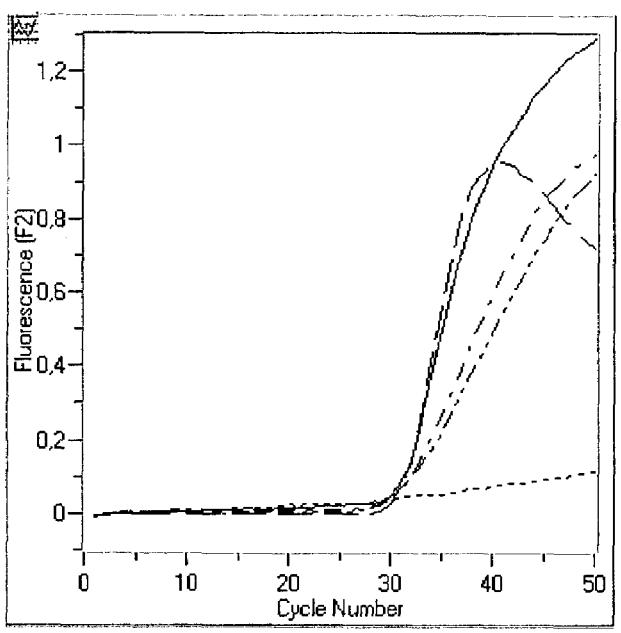
FIG. 3b: PBGD

Excessive Polymerase Enhances Amplification of Targets of Relatively Low Abundance in Multiplex PCR An assay according to example 1 was performed with increasing Polymerase concentrations. Either, $10^2$ copies of CK20 with a background PCR of $10^4$ copies of PBGD (FIG. 3a) or $10^4$ copies of PBGD with background PCR of $10^6$ copies CK20 (FIG. 3b) were quantified.

As shown in the figures, an increase of Polymerase concentration results an increase in the PCR exponential phase gradient of a multiplex PCR. This is in surprising contrast to what has been observed previously in a comparable monoplex set up (see example 2 above).

Moreover, the results show that a Polymerase concentration of 0.33 Units/µl is still not sufficient to equate the multiplex PCR exponential phase gradient to that of the individual PCR. In this experiment, it is only at an "excessive" amount of 0.66 units/µl Polymerase which results in a performance comparable to the monoplex control.

Further experiments with respect to the refinement of a general bona fide Polymerase concentration (data not shown) revealed that a Polymerase concentration of at least about 0.5 units/µl reaction volume is needed such that that the gradient of the multiplex PCR curve becomes equivalent to that of an individual PCR (data not shown).

EXAMPLE 5

Enhanced Performance of Hot Start Protocols Over Regular PCR Amplification

Hot start PCR cycling was done according to example 1 with the exceptions that for monoplex as well as for multiplex PCR, the reaction buffer and the modified Taq Polymerase from the LightCycler—FastStart DNA Master Hybridization Probes Kit (Roche Molecular Biochemicals, Cat No. 3 003 248) were used in comparison. Amplification of $10^4$ copies of PBGD was analyzed with a background PCR of $10^6$ copies CK 20 for enzyme concentrations of either 0.0825 U/µl, 0.165 U/µl, 0.33 U/µl or 0.66 U/µl Polymerase (final concentration). The thermocycling protocol was amended by initial heating at 94° C. for 10 minutes and 94° C. for 10 seconds during cycling.

Figure 4A:
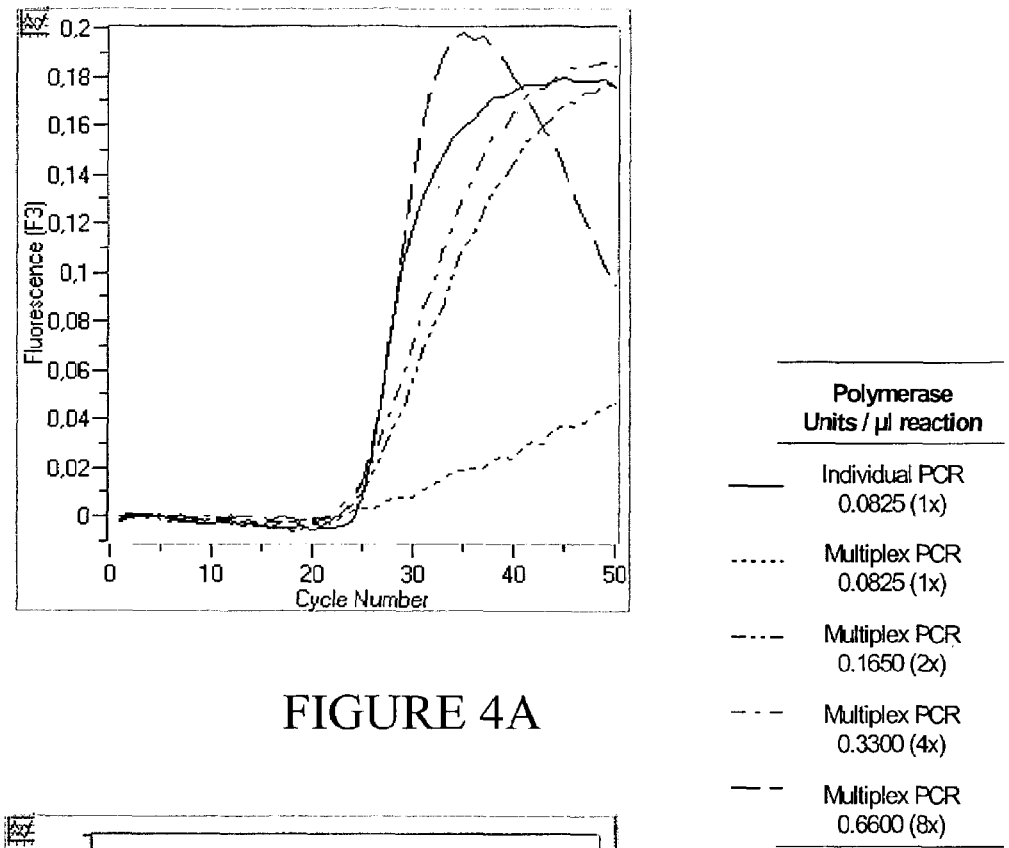
FIG. 4a: Taq DNA Polymerase
Figure 4B:
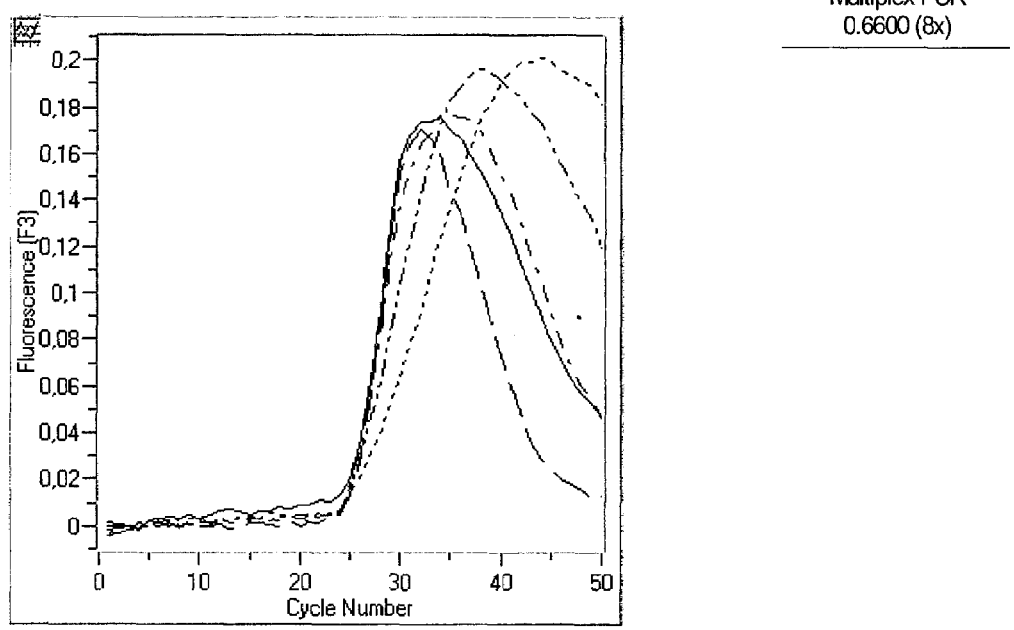
FIG. 4b: FastStart DNA Polymerase

FIG. 4 shows a comparison of the enzyme amounts required by a hot start Polymerase as compared to a regular Polymerase under identical titration conditions with the exception of the enzyme and its corresponding buffer. Whereas 0.66 Polymerase units/µl reaction volume of a regular Polymerase yields a multiplex PCR exponential phase gradient equivalent to an individual PCR (FIG. 4a), the use of a hot start Polymerase reduces the requirement by a factor of about 2 (FIG. 4b).

EXAMPLE 6

Potential Dynamic Range for Excessive Polymerase Multiplex PCR (Hot Start)

Figure 5A:
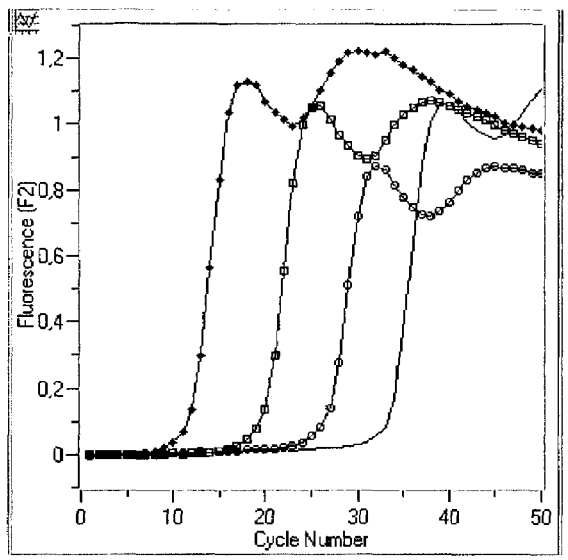
FIG. 5a: amplification of varying copy numbers of CK20 with a background of 100 copies PBGD
Figure 5B:
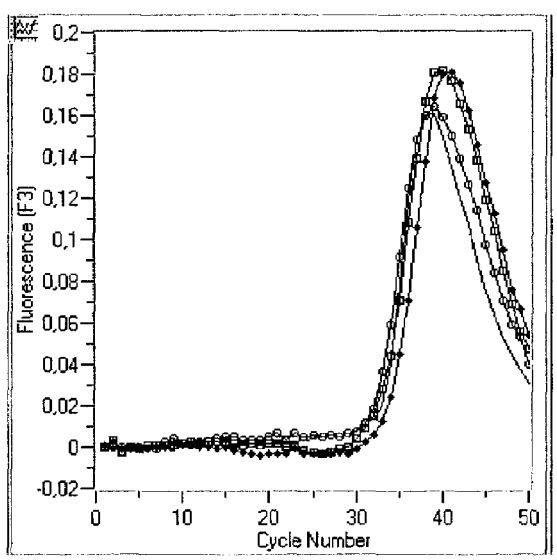
FIG. 5b: amplification of 100 copies PBGD with a background of varying copy numbers CK20
Figure 5C:
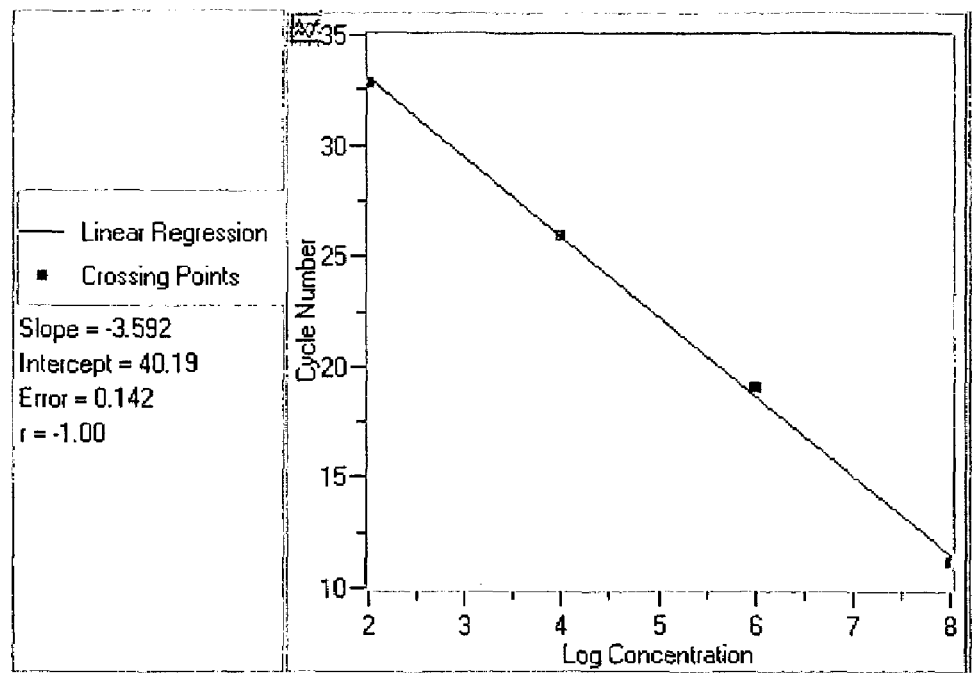
FIG. 5c: regression analysis of CK20 amplification

FIG. 5 show a multiplex experiment according to example 1 using FastStart Polymerase. PCR amplification of $10^2$ PBGD copies was performed with a respective background of $10^2$, $10^4$, $10^6$ and $10^8$ copies of CK20 and an excessive amount of 0.55 units/µl reaction volume FastStart Polymerase. As can be seen in the figure, the PBGD PCR exponential phase curve gradients (FIG. 5b) and the crossing points are similar to each other irrespective of the background CK20 PCR (FIG. 5a). For the CK20 PCR amplification, the linear relationship between crossing point and log concentration essential for accurate PCR quantification is maintained ($R^2=-1$) (FIG. 5c).

Thus, these data show, that for multiplex amplification of PBGD and CK20 according to the invention, a dynamic range of $10^6$ is obtained with the hot start embodiment.

EXAMPLE 7

Potential Dynamic Range for Excessive Polymerase Multiplex PCR (Hot Start)

Identical results have been obtained in a similar experiment with Her2/neu and beta Globin as different amplification targets. Amplification conditions were basically identical to those of example 1. In this case, however, PCR has been performed using 1 U Klentaq Polymerase (Clontech, corresponding to 6 U standard polymerase) in combination with KlenTaq Antibody (Clontech) under conditions suggested by the supplier as a means for hot start amplification according to the manufacturer's instructions.

The following primers according to Seq. Id. No. 9–10 for Her2/neu and Seq. Id. No. 11–12 for beta Globin have been used.

```
Her2/neu forward primer:
5'-CCTCTGACGTCCATCGTCTC-3'      (Seq. Id. No. 9)

Her2/neu reverse primer
5'-CGGATCTTCTGCTGCCGTCG-3'      (Seq. Id. No. 10)

β-globin forward primer:
5'-ACACAACTGTGTTCACTAGC-3'      (Seq. Id. No. 11)

β-globin reverse primer:
5'-CAACCTCATCCACGTTCACC-3'      (Sq. Id. No. 12)
```

Hybridization probes for Her2/neu were oligonucleotides comprising sequences according to Seq. Id. No. 13, 5' labeled with LC-Red 640 and Seq. Id. No. 14, 2' labeled with Fluorescein. Hybridization probes for beta Globin were oligonucleotides comprising sequences according to Seq. Id. No. 15, 5' labeled with LC-Red 705 and Seq. Id. No. 16, 3' labeled with Fluorescein:

```
Her2neu:
5'-Red 640-ACCAGCAGAATGCCAACCA-Phosphate-3'               (Seq. Id. No. 13)

5'-CTTGATGAGGATCCCAAAGACCACCCCCAAGACCAC-Fluorecein-3'     (Seq. Id. No. 14)

β-globin:
5'-Red 705-AGACTTCTCCTCAGGAGTCAGGTGCACCATG-Phosphate-3'   (Seq. Id. No. 15)

5'-CCACAGGGCAGTAACGG-Fluorecein-3                         (Seq. Id. No. 16)
```

In this experiment, 10 copies of Her2/neu plasmid DNA could be amplified with identical efficiency regardless of a background of $10$–$10^7$ copies of beta Globin plasmid DNA, corresponding to a dynamic range of $10^6$.

EXAMPLE 8

Independence of Dynamic Range Obtained by Addition of Excess Polymerase from Absolute Target Copy Numbers In order to assess the capacities of excessive Polymerase multiplex hot start PCR, and further, in order to exclude a potential dependence of the dynamic range from absolute target concentrations, an experiment was performed basically according to the conditions disclosed in example 1 with some minor alterations:

More precisely, $10^2$ copies of PBGD were amplified with a background PCR of $10^2$, $10^4$, $10^6$ and $10^8$ copies of CK20 with varying amounts of FastStart polymerase and analyzed under the same conditions.

As an indicator for quantititive amplification of PBDG, crossing points (cp values) were determined using the so called "second derivative algorithm" (U.S. Pat. No. 6,303,305) according to the RocheLightCycler manual (Roche Molecular Biochemicals). Using the second derivative data processing algorithm, within an expected statistical tolerance, identical cp values were obtained for a given target concentration independently from the excess of CK 20 added, provided that an enzyme concentration according to the invention was used.

The cp values for PBDG obtained are indicated in the following table:

TABLE 1

| | cp values for PBDG | | | |
|---|---|---|---|---|
| | $10^2$ Copies PBGD 0.0412 Units/µl | $10^2$ Copies PBGD 0.0825 Units/µl | $10^2$ Copies PBGD 0.1650 Units/µl | $10^2$ Copies PBGD 0.3300 Units/µl |
| $10^2$ Copies CK20 | cp: 31.44 | cp: 31.98 | cp: 32.12 | cp: 33.16 |
| $10^4$ Copies CK20 | cp: 31.23 | cp: 32.02 | cp: 31.53 | cp: 31.89 |
| $10^6$ Copies CK20 | cp: – | cp: >46 | cp: 34.35 | cp: 32.12 |
| $10^8$ Copies CK20 | cp: – | cp: – | cp: 38.88 | cp: 32.65 |

From these results, it is reasonable to draw the following conclusions:

First, the data obtained for an enzyme concentration according to the invention (table 1, right column, 0.3300 U/µl) demonstrate that in this case a multiplex PCR according to the invention results in an overall dynamic range of $10^6$, provided that the target nucleic acids to be amplified within the multiplex assay are present in copy numbers between $10^2$ and $10^8$.

Second, it is trivial that under identical experimental conditions $10^4$ copies of PBDG would have been amplified with the same amplification efficiency as it is the case for $10^2$ copies of PBDG. If then, the result of amplifying $10^2$ copies of PBDG in the background of $10^6$ copies of CK20 is compared with an amplification of $10^4$ copies in the background $10^8$ copies of CK20 (not shown), it can also be concluded, that the effect of increase of the dynamic range upon inventive usage of excess amounts of Polymerase is independent from the absolute copy numbers of target DNA originally present in the sample.

LIST OF REFERENCES

Bernard, P. S., et al., Anal Biochem 255 (1998) 101–7
Bercovich, D., et al., Biotechniques 27 (1999) 762–770
Bieche, I., et al., Cancer Res 59 (1999) 2759–65
Director-Myska, A. E., et al., Environ Mol Mutagen 37 (2001) 147–54
Gibson, U. E., et al., Genome Res 6 (1996) 995–1001
Halminen, M., et al., Cytokine 11 (1999) 87–93
Kainz, P., et al., Biotechniques 28 (2000) 278–82
Kellogg, D. E., et al., Biotechniques 16 (1994) 1134–7
Lin, Y. Jayasena, S. D., J Mol Biol 271 (1997) 100–11
Meijerink, J., et al., J Mol Diagn 3 (2001) 55–61
Moretti, T., et al., Biotechniques 25 (1998) 716–22
Sharkey, D. J., et al., Biotechnology (NY) 12 (1994) 506–9
Tucker, R. A., et al., Mol Diagn 6 (2001) 39–47

Vet, J. A., et al., Proc Natl Acad Sci U S A 96 (1999) 6394–9
U.S. Pat. No. 5,118,801
U.S. Pat. No. 5,677,152
U.S. Pat. No. 5,693,502
U.S. Pat. No. 6,174,670
U.S. Pat. No. 6,303,305
WO97/46706
WO97/46707
WO97/46712

What is claimed:

1. A method for measuring amounts of at least two mRNAs in a sample by multiplex PCR, comprising the steps of:

incubating said at least two mRNAs with a reverse transcriptase under conditions effective to produce a single-stranded cDNA from each mRNA, wherein at least one high-abundance mRNA is present in at least a 100-fold molar excess over at least one low-abundance mRNA, and wherein said mRNAs are present in copy numbers between $10^2$ and $10^8$;

amplifying said single-stranded cDNAs with a thermostable DNA polymerase at a concentration of at least 0.5 units DNA polymerase/μl and a pair of primers for each single-stranded cDNA under conditions effective to amplify said single-stranded cDNAs in a real-time polymerase chain reaction, whereby the amplification of said low-concentration mRNA is inhibited in the presence of said high-concentration mRNA by not more than 10%, relative to amplification in the absence of said high-concentration mRNA;

determining the amount of each of said amplified single-stranded cDNAs by real-time measurement of an amount of fluorescent emission, wherein the amount of fluorescent emission provides a quantitative value of the amount of said amplified single-stranded cDNA; and determining the amount of each of said mRNAs in said sample from the amount of said cDNA derived from said mRNA.

2. The method of claim 1, wherein said step of incubating said single-stranded cDNAs with a thermostable DNA polymerase is performed using a hot start technique.

3. The method of claim 2, wherein said thermostable DNA polymerase is modified with a heat labile blocking group.

4. The method of claim 2, wherein said thermostable DNA polymerase is inactivated at ambient temperatures by addition of oligonucleotide aptamers.

5. The method of claim 2, wherein said thermostable DNA polymerase is inactivated at ambient temperatures by addition of an anti-DNA polymerase antibody, said antibody binding to said polymerase and inhibiting polymerization by said polymerase at temperatures below those of said real-time polymerase chain reaction, said antibody further being releasable from said polymerase at temperatures of said real-time polymerase chain reaction.

6. The method of claim 1, wherein said fluorescent emission is obtained by excitation of a single-stranded nucleic acid probe labeled with a fluorescent moiety and incubated with said single-stranded cDNAs.

7. The method of claim 1, wherein said fluorescent emission is obtained by excitation of at least one pair of FRET hybridization probes labeled with a fluorescent moiety and incubated with said single-stranded cDNAs.

8. The method of claim 1, wherein said fluorescent emission is obtained by excitation of at least one TaqMan hybridization probe labeled with a fluorescent moiety and incubated with said single-stranded cDNAs, and said thermostable DNA polymerase has 5'–3' exonuclease activity.

9. The method of claim 1, wherein said fluorescent emission is obtained by excitation of at least one molecular beacon labeled with a fluorescent moiety and incubated with said single-stranded cDNAs.

10. The method of claim 1, wherein said step of amplifying said single-stranded cDNAs is performed for less than one minute per amplification cycle.

* * * * *

UNITED STATES PATENT AND TRADEMARK OFFICE
CERTIFICATE OF CORRECTION

| | | |
|---|---|---|
| PATENT NO. | : 7,118,867 B2 | Page 1 of 1 |
| APPLICATION NO. | : 10/300576 | |
| DATED | : October 10, 2006 | |
| INVENTOR(S) | : Tabiti et al. | |

It is certified that error appears in the above-identified patent and that said Letters Patent is hereby corrected as shown below:

On the Title page Item (75) Inventors:

change "Hallegh Page Millward" to --Haleigh Page Millward--

Signed and Sealed this

Nineteenth Day of December, 2006

JON W. DUDAS
*Director of the United States Patent and Trademark Office*

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:CK20 forward primer

<400> SEQUENCE: 1
atcaagcagt ggtacgaaac                                                    20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:CK20 reverse primer

<400> SEQUENCE: 2
aggacacacc gagcattt                                                      18

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:CK20 probe1

<400> SEQUENCE: 3
attacagaca aattgaagag ctgcg                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:CK20 probe 2

<400> SEQUENCE: 4
agtcagatta aggatgctca actgc                                              25

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:PBGD forward primer

<400> SEQUENCE: 5
gcggagccat gtctggtaa                                                     19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PBGD reverse
      primer

<400> SEQUENCE: 6
ccagggtacg aggctttcaa                                              20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:PBGD probe 1

<400> SEQUENCE: 7
gagagtgatt cgcgtgggta cccg                                         24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:PBGD probe 2

<400> SEQUENCE: 8
agagccagct tgctcgcata cagac                                        25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Her2/neu
      forward primer

<400> SEQUENCE: 9
cctctgacgt ccatcgtctc                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Her2/neu
      reverse primer

<400> SEQUENCE: 10
cggatcttct gctgccgtcg                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: -globin
      forward primer

<400> SEQUENCE: 11
acacaactgt gttcactagc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:a-globin
      reverse primer

```
<400> SEQUENCE: 12
caacctcatc cacgttcacc                                                    20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence:
      hybridization probe

<400> SEQUENCE: 13
accagcagaa tgccaacca                                                     19

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence:
      hybridization probe

<400> SEQUENCE: 14
cttgatgagg atcccaaaga ccaccccaa gaccac                                   36

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:
      hybridization probe

<400> SEQUENCE: 15
agacttctcc tcaggagtca ggtgcaccat g                                       31

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:
      hybridization probe

<400> SEQUENCE: 16
ccacagggca gtaacgg                                                       17
```